United States Patent [19]
Oakley et al.

[11] Patent Number: 6,080,474
[45] Date of Patent: Jun. 27, 2000

[54] POLYMERIC ARTICLES HAVING IMPROVED CUT-RESISTANCE

[75] Inventors: Ehteridge Odell Oakley, Matthews; Gregory J. Johnson, Charlotte, both of N.C.; Herman Leslie Lanieve, Warren, N.J.

[73] Assignee: Hoechst Celanese Corporation, Warren, N.J.

[21] Appl. No.: 08/947,170

[22] Filed: Oct. 8, 1997

[51] Int. Cl.⁷ ..................................................... B32B 5/16
[52] U.S. Cl. .......................... 428/323; 428/206; 428/208; 428/217; 428/325; 428/329; 428/365; 428/496; 428/908.8
[58] Field of Search ..................................... 428/323, 325, 428/206, 208, 217, 496, 908.8, 365, 329

[56] References Cited

U.S. PATENT DOCUMENTS

| | | |
|---|---|---|
| 2,328,105 | 8/1943 | Strobino . |
| 3,185,751 | 5/1965 | Sutton . |
| 3,793,648 | 2/1974 | Dorre et al. ................................. 2/2.5 |
| 4,004,295 | 1/1977 | Byrnes, Sr. . |
| 4,384,449 | 5/1983 | Byrnes, Sr. et al. . |
| 4,436,130 | 3/1984 | Suzuki et al. . |
| 4,470,251 | 9/1984 | Bettcher . |
| 4,936,085 | 6/1990 | Kolmes et al. ............................. 57/229 |
| 5,020,161 | 6/1991 | Lewis, Jr. et al. . |
| 5,051,301 | 9/1991 | Singh et al. . |
| 5,087,499 | 2/1992 | Sullivan . |
| 5,113,532 | 5/1992 | Sutton . |
| 5,119,512 | 6/1992 | Dunbar et al. . |
| 5,146,628 | 9/1992 | Herrmann et al. . |
| 5,200,263 | 4/1993 | Gould et al. . |
| 5,224,363 | 7/1993 | Sutton . |
| 5,327,954 | 7/1994 | Nakamura . |
| 5,368,930 | 11/1994 | Samples ................................... 428/323 |
| 5,442,815 | 8/1995 | Cordova et al. ............................ 2/161 |
| 5,489,476 | 2/1996 | Dischler ................................... 428/400 |
| 5,490,550 | 2/1996 | Massie, II et al. . |
| 5,568,657 | 10/1996 | Cordova et al. ............................ 2/167 |
| 5,597,649 | 1/1997 | Sandor et al. ........................... 428/370 |
| 5,738,940 | 4/1998 | Neuert . |
| 5,817,433 | 10/1998 | Darras ..................................... 428/911 |
| 5,822,791 | 10/1998 | Baris ........................................... 2/2.5 |

FOREIGN PATENT DOCUMENTS

| | | |
|---|---|---|
| 0 458 343 A1 | 11/1991 | European Pat. Off. . |
| 0 790 335 | 8/1997 | European Pat. Off. . |
| 22 61 754 | 6/1974 | Germany . |
| 24 50 959 | 5/1976 | Germany . |
| 55-55109 | of 1980 | Japan . |
| 3-130413 | of 1991 | Japan . |
| 145592 | 12/1988 | Poland . |
| 1 492 332 | 10/1975 | United Kingdom . |
| 2 080 702 | 2/1982 | United Kingdom . |
| 94 09656 | 5/1994 | WIPO . |
| 95 31593 | 11/1995 | WIPO . |
| 97 07859 | 3/1997 | WIPO . |

OTHER PUBLICATIONS

Turek, et al., "Magnetic Fibers," *Journal of Magnetism and Magnetic Materials*, 83 (1990) pp. 279–280.

*Primary Examiner*—Hoa T. Le
*Attorney, Agent, or Firm*—Alston & Bird LLP

[57] ABSTRACT

A polymeric article having improved cut-resistance is composed of (A) an initial polymeric article having cut-resistant properties; and (B) a cut-resistant elastomeric coating disposed on an outer surface of the initial polymeric article, wherein the elastomeric coating is composed of an elastomer and a hard filler distributed in the elastomer. The hard filler has a Mohs Hardness value of at least about 3. The final polymeric article has improved cut-resistance, improved flexibility, and improved comfort and will retain its properties when routinely laundered. The article is preferably in the form of a polymeric textile article, more preferably in the form of an elastomeric protective garment, and most preferably in the form of gloves, e.g., surgical gloves.

44 Claims, No Drawings

POLYMERIC ARTICLES HAVING IMPROVED CUT-RESISTANCE

BACKGROUND OF THE INVENTION

This invention relates to polymeric articles. More particularly, this invention relates to polymeric articles having improved cut-resistance.

Polymeric articles, particularly elastomeric textile articles, having improved resistance to cutting with a sharp edge have long been sought. Elastomeric textile articles in the form of protective garments, particularly gloves, with improved cut-resistance are especially desired. Cut-resistant gloves have many uses. For example, cut-resistant gloves are useful for meat processing personnel exposed to sharp knives, for metal and glass handlers who must be protected from sharp edges during the handling of materials, and for medical personnel who are exposed to scalpels and other sharp instruments.

Cut-resistant gloves are known in the art. Reference is made, for example, to U.S. Pat. Nos. 4,004,295, 4,384,449 and 4,470,251 and to EP 458,343. These references teach cut-resistant gloves which have been made from yarn containing flexible metal wire or highly oriented fibers having high modulus and high tensile strength, such as aramids, thermotropic liquid crystalline polymers, and extended chain polyethylene.

A drawback to gloves made from yarn containing flexible metal wire is hand fatigue with resultant decreased productivity and increased likelihood of injury. Moreover, with extended wear and flexing, the wire may fatigue and break, causing cuts and abrasions to the hands. In addition, the wire will act as a heat sink when a laundered glove is dried at elevated temperatures, which may reduce tensile strength of the yarn or fiber, thereby decreasing glove protection and glove life.

Therefore, cut-resistant gloves which do not use metal wire are desired.

Polymers have been mixed with particulate matter and made into fibers, but not in a way that significantly improves the cut-resistance of the fiber. For example, small amounts of particulate titanium dioxide have been used in polyester fiber as a delustrant. Also used in polyester fibers are small amounts of colloidal silicon dioxide, which is used to improve gloss. Magnetic materials have been incorporated into fibers to yield magnetic fibers. Examples include: cobalt/rare earth element intermetallics in thermoplastic fibers, as in published Japanese Patent Application No. 551098909 (1980); cobalt/rare earth element intermetallics or strontium ferrite in core-sheath fibers, described in published Japanese Patent Application No. 3-130413 (1991); and magnetic materials in thermoplastic polymers, described in Polish Patent No. 251,452 and also in K. Turek et al., J. Magn. Magn. Mater (1990), 83 (1–3), pp. 279–280.

Various kinds of gloves have been made in which metal has been included in the fabrication of the glove to impart protective qualities to the glove. For example, U.S. Pat. Nos. 2,328,105 and 3,185,751 teach that a flexible, X-ray shield glove may be made by treating sheets of a suitable porous material with a finely divided, heavy metal which may be lead, barium, bismuth or tungsten, or may be made from a latex or dispersion containing heavy metal particles. U.S. Pat. No. 5,020,161 discloses gloves which are resistant to corrosive liquids wherein the gloves have been made with a metal film layer. However, the gloves disclosed in the aforementioned references also do not appear to have significantly improved cut-resistance.

Cut-resistant textile articles are also disclosed, for example, in U.S. Pat. Nos. 5,200,263; 5,119,512; 5,146,628; and 5,224,363.

U.S. Pat. No. 5,200,263 teaches a puncture- and cut-resistant composite material and articles, e.g., gloves, made therefrom, wherein the composite material is composed of at least one elastomer layer containing a plurality of platelets oriented substantially parallel to the plane of the elastomeric layer, each of the platelets being a small, thin element substantially impervious to normally encountered puncturing and/or cutting by sharp instruments.

U.S. Pat. No. 5,119,512 discloses cut-resistant yarn and fabrics and gloves made therefrom. The reference further teaches a cut-resistant article composed of a cut-resistant jacket surrounding a less cut-resistant member. The cut-resistant jacket contains a fabric made from a yarn containing at least one high strength, longitudinal strand wrapped with a fiber. The less cut-resistant member is a rope, webbing, strap, hose or inflatable structure. The reference further teaches a highly cut-resistant composite yarn composed of at least two fibrous materials, wherein at least one fibrous material is cut-resistant and at least one fibrous material has a high level of hardness.

U.S. Pat. No. 5,224,363 discloses cut-resistant protective garments, e.g., gloves, which are formed from high strength composite strands. The composite strands contain a cut-resistant core material coated with a fluid impervious material. The cut-resistant core material may be Kevlar, aramid strands, stainless steel strands, or a combination of Kevlar and stainless steel strands. The fluid impervious coating may be polyurethane or vinyl.

U.S. Pat. No. 5,146,628 discloses protective gloves coated with a polyurethane material. The polyurethane coating is abrasion resistant, cut-resistant, flexible and soft and provides the glove with slip-resistant and gripping properties.

Puncture-resistant textile articles are also known in the art. Reference is made, e.g., to U.S. Pat. Nos. 5,363,930 and 5,087,499.

U.S. Pat. No. 5,363,930 teaches a thin elastomeric sheet material and protective clothing, e.g., gloves, made therefrom. The elastomeric sheet material has enhanced puncture-resistance and is prepared by embedding thin plate-like non-elastomeric particles in an elastomeric matrix. The preferred non-elastomeric particles have a hardness on the Mohs scale of at least 5 and include metals, ceramics and crystalline minerals.

U.S. Pat. No. 5,087,499 discloses puncture-resistant and medicinal treatment garments, e.g., gloves, formed from fibers such as Kevlar® or Spectra®. The fibers may be coated with an abrasive material such as, e.g., a mixture of ceramic or metallic particles and a polymeric resin.

U.S. Pat. No. 5,051,301 discloses composites and textile articles made therefrom, wherein the composites have improved toughness and contain a ceramic matrix and a plurality of layers of boron nitride-coated fibrous material. The ceramic matrix may be used in combination with an organic binding material.

Copending, commonly assigned U.S. patent application Ser. No. 08/752,297, filed Nov. 19, 1996, discloses the manufacture of cut-resistant garments such as gloves from cut-resistant fibers.

Although cut-resistant gloves are known in the art, it is continually desirable to increase the cut-resistance of such gloves.

In addition, it would be desirable to provide gloves with improved flexibility and comfort as well as increased cut-resistance. It would further be desirable to provide cut-resistant gloves which retain their properties when routinely laundered.

Accordingly, a primary object of this invention is to provide polymeric articles with improved cut-resistance.

A further object of this invention is to provide polymeric textile articles, such as protective garments, with improved cut-resistance.

Another object of this invention is to provide gloves having improved cut-resistance.

Yet another object of this invention is to provide gloves having improved cut-resistance and improved flexibility, are more comfortable and which retain their properties when routinely laundered.

A further object of this invention is to provide a method of improving the cut-resistance of a cut-resistant polymeric product.

Another object of this invention is to provide a method of improving the cut-resistance of a cut-resistant polymeric textile product such as a protective garment.

Yet another object of this invention is to provide a method of improving the cut-resistance of cut-resistant gloves.

These and other objects which are achieved according to the present invention can be discerned from the following description.

SUMMARY OF THE INVENTION

The present invention is directed to a polymeric article having improved cut-resistance, containing:

(A) an initial polymeric article having initial cut-resistant properties; and (B) a cut-resistant elastomeric coating disposed on an outer surface of the initial polymeric article, wherein the elastomeric coating is composed of an elastomer and a hard filler distributed in the elastomer, the hard filler having a Mohs Hardness value of at least about 3, thereby providing a final polymeric article having improved cut-resistance.

In preferred embodiments of the invention, the initial cut-resistant polymeric article is a flexible, cut-resistant polymeric article, more preferably, a flexible, cut-resistant textile article, most preferably a flexible, cut-resistant protective garment.

Also in preferred embodiments of the invention, the initial article is formed from cut-resistant fibers formed from fiber-forming polymers and hard fillers distributed in such polymers. The initial article may also be a nonwoven textile fabric containing particles in the fibers or without hard particles.

The initial article may also be an elastomeric article with or without hard particles, e.g., surgical gloves.

A second embodiment of this invention is directed to a method of improving the cut-resistance of an initial cut-resistant polymeric article involving the step of applying the above-described cut-resistant elastomeric coating to an outer surface of the initial cut-resistant article, thereby forming a final polymeric article having improved cut-resistance.

The polymeric articles provided by the present invention have improved cut-resistance, improved comfort and improved flexibility. In addition, these articles will retain their properties when laundered.

DETAILED DESCRIPTION OF THE INVENTION

The present invention provides a polymeric article having improved cut-resistance. This invention also provides a method of improving the cut-resistance of polymeric articles which are already cut-resistant.

The polymeric article of this invention is composed of an initial cut-resistant polymeric article and an elastomeric cut-resistant coating disposed on an outer surface of the initial polymeric article. The combination of the initial polymeric article and the elastomeric coating disposed thereon constitutes the polymeric article of this invention which is sometimes referred to herein as "the final polymeric product". The elastomeric cut-resistant coating is composed of an elastomer and a first hard filler distributed in the elastomer. The first hard filler has a Mohs Hardness value of at least about 3. The final polymeric article, which is the polymeric article of this invention, has more cut-resistance than an article formed by coating the initial polymeric article with an unfilled elastomer material.

As stated above, the cut-resistant elastomeric coating disposed on the initial polymeric cut-resistant article contains an elastomeric polymer having a hard filler distributed therein.

Non-limiting examples of suitable elastomeric polymers which can be used in the cut-resistant coating include natural rubber, synthetic rubber and thermoplastic elastomers. Specific examples of suitable elastomeric polymers include, e.g., polyvinyl chloride, polyurethane, nitrile rubber, vinyl rubber, polyisoprene, neoprene, chloroprene, and silicone rubber. Preferred elastomeric polymers for use in this invention include polyurethane, polyvinyl chloride and silicone rubber.

The hard filler distributed in the elastomer polymer of the coating used in this invention has a Mohs Hardness value of at least about 3, more preferably at least about 4 and most preferably at least about 5.

In preferred embodiments of this invention, the hard filler in the elastomer polymer of the cut-resistant coating is in the form of particles. The hard filler particles may be in the form of flat particles (i.e., platelets), elongated particles (i.e., needles), irregularly-shaped particles, or round particles. Preferably, the hard filler particles are in the form of platelets because platelets are more efficient in imparting cut-resistance.

The particle size of the hard filler particles preferably ranges from about 1 to about 5 microns. For flat or elongated particles, the particle size refers to the length along the long axis of the particle (i.e. the long dimension of an elongated particle or the average diameter of the face of a platelet).

The hard filler distributed in the elastomer polymer is preferably a metal or metal alloy, a ceramic material or a crystalline mineral. Suitable metals include, e.g., tungsten, copper, brass, bronze, aluminum, steel, iron, monel, cobalt, titanium, magnesium, silver, molybdenum, tin and zinc. Non-limiting examples of suitable crystalline minerals include baddeleyite, chloritoid, clinozoisite, chondrodite, euclasite, petalite, sapphire, spodumene, staurolite, and clay. Suitable ceramic materials include, e.g., glass and alumina. Most preferably, the hard filler used in the elastomeric coating of this invention is alumina.

The hard filler may be added to the elastomer by any of the standard methods of adding a filler to a resin. For example, the combining of the hard filler and the elastomer can be carried out in an extruder, e.g., a twin screw extruder, by mixing the hard filler with molten elastomer under conditions sufficient to provide a uniform distribution of the filler in the elastomer. The hard filler may also be present during the manufacture of the elastomer.

The elastomer coating preferably contains from about 1% to about 15% by weight of the hard filler therein.

The elastomer coating may also contain conventional additives such as, e.g., thickening agents.

The elastomeric coating used in the present invention preferably has a thickness of from about 2 to about 3 millimeters.

As will be discussed in greater detail later herein, the cut-resistant elastomeric coating may be applied to the initial elastomeric article using any of a variety of methods. Preferred among these are dipping, spraying, flowing, rolling, brushing, partial coating, dotting, and strudeling in lines or zig-zag patterns, with dipping being more preferred.

The initial polymeric article used in the present invention is a cut-resistant polymeric article, preferably a flexible, cut-resistant polymeric article. The initial cut-resistant polymeric article may be any of the cut-resistant articles known in the art. Preferably, the initial cut-resistant polymeric article is a polymeric textile article, more preferably a protective garment and most preferably gloves, e.g., surgical gloves. Suitable cut-resistant gloves which can be used as the initial polymeric cut-resistant article in the present invention include those disclosed, for example, in U.S. Pat. Nos. 5,200,263; 5,119,512; 5,146,628; and 5,224,363; each of the foregoing references being hereby incorporated by reference herein in their entirety.

In the most preferred embodiment of this invention, the initial polymeric cut-resistant article is made from a cut-resistant fiber as disclosed in copending, commonly assigned U.S. patent application Ser. No. 08/752,297, filed Nov. 19, 1996, which is hereby incorporated by reference herein. Such cut-resistant fiber is formed from a fiber-forming polymer and a hard filler distributed in the fiber-forming polymer.

As used herein, the term "fiber" includes not only conventional single fibers and filaments, but also yarns made from a multiplicity of these fibers. In general, yarns are used to make apparel, fabrics and the like.

The fiber-forming polymer is preferably melt-processable (i.e., the polymer will melt in a temperature range which makes it possible to spin the polymer into fibers in the melt phase without significant decomposition), in which case the cut-resistant fiber is made by melt spinning. For polymers which cannot be spun into fibers in the melt, wet spinning and dry spinning may also be used to produce the cut-resistant fiber.

Amorphous polymers, semi-crystalline polymers, and liquid crystalline polymers may all be used to form the cut-resistant fiber used in this invention. Of these, semi-crystalline and liquid crystalline polymers are preferred.

A particularly preferred fiber-forming polymer is an isotropic semi-crystalline polymer. "Isotropic" refers to polymers which are not liquid crystalline polymers, which are anisotropic. Preferably, the isotropic semi-crystalline polymer is melt-processable. Non-limiting examples of highly useful semi-crystalline polymers include poly(alkylene terephthalates), poly(alkylene naphthalates), poly(arylene sulfides), aliphatic and aliphatic-aromatic polyamides, and polyesters comprising monomer units derived from cyclohexanedimethanol and terephthalic acid. Examples of specific semi-crystalline polymers include poly(ethylene terephthalate), poly(butylene terephthalate), poly(ethylene naphthalate), poly(phenylene sulfide), poly(1,4-cyclohexanedimethanol terephthalate) (wherein the 1,4-cyclohexanedimethanol is a mixture of cis and trans isomers), nylon 6 and nylon 66. Polyolefins, particularly polyethylene and polypropylene, are other semi-crystalline polymers that may be used as the fiber-forming polymer.

Extended chain polyethylene, which has a high tensile modulus, is made by the gel spinning or the melt spinning of very high or ultrahigh molecular weight polyethylene. Extended chain polyethylene already has a high cut-resistance, but can be made even more cut-resistant by adding particles to the fiber.

The preferred semi-crystalline isotropic polymer for use as the fiber-forming polymer is poly(ethylene terephthalate).

The fiber-forming polymer may also be a liquid crystalline polymer (LCP). LCPs give fibers with very high tensile strength and/or modulus. The liquid crystalline polymer may be processable in the melt (i.e., thermotropic), in which case melt spinning is the preferred method of making the fiber. However, polymers which cannot be processed in the melt may also be utilized. Thus, polymers that exhibit liquid crystalline behavior in solution can be blended with a hard filler and then wet or dry spun to yield cut-resistant fibers. For example, the aromatic polyamide made from p-phenylenediamine and terephthalic acid (as for example polymers sold under the KEVLAR® trademark) can be filled and wet spun (i.e. by dry-jet wet-spinning from a concentrated sulfuric acid solution) to yield a cut-resistant fiber, provided that the hard filler does not react with or dissolve in the solvent. Other aromatic polyamides that are soluble in polar aprotic solvents, such as N-methylpyrrolidinone, may also be spun into cut-resistant fibers. These aromatic polyamides may not be liquid crystalline under some or all conditions, but they still yield high modulus fibers. Some may exhibit lyotropic liquid crystalline phases at some concentrations and in some solvents, but isotropic solutions at other concentrations or in other solvents.

The preferred liquid crystalline polymers (LCPS) for use as fiber-forming polymers are thermotropic LCPs. Non-limiting examples of suitable thermotropic LCPs include aromatic polyesters, aliphatic-aromatic polyesters, aromatic poly(esteramides), aliphatic-aromatic poly(esteramides), aromatic poly(esterimides), aromatic poly(estercarbonates), aromatic polyamides, aliphatic-aromatic polyamides and poly(azomethines). The preferred thermotropic LCPs are aromatic polyesters and poly(esteramides) which form liquid crystalline melt phases at temperatures less than about 360° C. and include one or more monomer units derived from terephthalic acid, isophthalic acid, 1,4-hydroquinone, resorcinol, 4,4'-dihydroxybiphenyl, 4,4'-biphenyldicarboxylic acid, 4-hydroxybenzoic acid, 6-hydroxy-2-naphthoic acid, 2,6-naphthalenedicarboxylic acid, 2,6-dihydroxynaphthalene, 4-aminophenol, and 4-aminobenzoic acid. Some of the aromatic groups may include substituents which do not react under the conditions of the polymerization, such as, e.g., lower alkyl groups having 1–4 carbons, aromatic groups, fluorine, chlorine, bromine and iodine.

All of the above-listed fiber-forming polymers are known to be useful for making fibers and all are commercially available.

The fiber-forming polymer used to form the cut resistant fiber contains a hard filler that imparts cut-resistance to the fiber formed therefrom. The hard filler used in the fiber-forming polymer preferably has Mohs Hardness value of at least about 3, more preferably at least about 4, and most preferably at least about 5.

The hard filler used in the fiber-forming polymer may be in the same form and of the same type as the hard filler used in the elastomeric coating of the final polymeric article of this invention.

The hard filler used in the fiber-forming polymer may be a metal, a metal alloy, a ceramic or a crystalline material. The metals, metal alloys, ceramics and crystalline materials recited previously herein as being suitable for use as the hard filler in the elastomeric polymer of the coating are also suitable for use as the hard filler in the fiber-forming polymer.

Iron, steel, tungsten and nickel are examples of metals and metal alloys suitable for use as the hard filler in the fiber-forming polymer. Of these, tungsten, which has a Mohs Hardness value of from about 6.5 to 7.5, is preferred. Non-limiting examples of other fillers which can be used as the hard filler in the fiber-forming polymer include metal oxides (such as aluminum oxide), metal carbides (such as tungsten carbide), metal nitrides, metal sulfides, metal silicates, metal silicides, metal sulfates, metal phosphates, and metal borides. Other examples of suitable hard fillers include silicon dioxide and silicon carbide. Titanium dioxide and silicon dioxide are less preferred if the fiber-forming polymer is a semi-crystalline polymer.

The particle size, particle size distribution, and the quantity of particles are all important parameters in obtaining good cut-resistance of the fiber while preserving the mechanical properties of the fiber. A particulate form of the filler may be used, with a powder form being generally suitable. Platelet particles and needle particles can also be utilized.

Selection of an appropriate particle size depends on the processing and on the fiber diameter. The filler particles should be small enough to easily pass through the spinneret apertures. The particles should also be small enough that the fiber's tensile properties do not appreciably deteriorate. For textile fibers, (i.e. fibers having a denier in the range of about 1.5 to about 15 dpf), the particles should be filtered or sieved in such a way that particles larger than about 6 microns are excluded. In general, the particles should have an average diameter of less than about 20 microns, preferably in the range of about 0.05 to about 5 microns and in specific cases, about 0.2 to about 2 microns. For elongated particles, the long dimension should fit through the spinneret holes. Therefore, the average particle length of an elongated particle should be less than about 20 microns, and preferably is in the range of about 0.05 to about 5 microns and in specific cases, about 0.2 to 2 microns.

The amount of hard filler used in the fiber-forming polymer is that amount which will yield enhanced cut-resistance without causing a significant loss of tensile properties. Specifically, the amount of hard filler used in the fiber-forming polymer is preferably that amount which will increase the cut-resistance of the fiber by at least 10%, as determined by ASTM F1790 (also known as the "Ashland Cut Protection Performance Test") or other tests generally accepted in the industry. More preferably, the amount of filler used is that amount which will increase the cut-resistance of the fiber by at least 20%, even more preferably by at least 35% and most preferably by at least 50%, as measured by the aforementioned tests, particularly ASTM F1790.

The amount of hard filler used in the fiber-forming polymer should not be such as to decrease the tensile properties of the fiber (tenacity and modulus) by more than about 50%. More preferably, the amount of filler used should not decrease the tensile properties of the fiber by more than about 25%. Most preferably, the amount of hard filler used should be such that there will not be a significant change in the fiber's tensile properties (i.e., less than about 10% decrease in properties).

On a weight basis, the filler is present in the fiber-forming polymer in an amount of preferably from about 0.05% to about 20%, more preferably from about 0.1% to about 20%. On a volume basis, the amount of filler in the fiber-forming polymer is preferably in the range of from about 0.01% to about 3.0%, more preferably from about 0.03% to about 3.0%, and most preferably from about 1.0% to about 3.0%, with the proviso that the amount of filler is within the weight ranges stated previously. Thus, for a dense filler, such as tungsten powder, in poly(ethylene terephthalate), the amount of filler corresponding to the volume percentages stated above but expressed on a weight basis, is preferably in the range of from about 0.14% to about 20% by weight, more preferably in the range of from about 0.42% to about 20% by weight, and most preferably in the range of from about 0.7% to about 14% by weight. For PET, good cut-resistant properties are obtained with about 0.7% by volume of tungsten filler, corresponding to about 10% by weight of tungsten filler. For thermotropic liquid crystalline polymers, improved cut-resistance can be obtained with from about 0.07% to about 0.14% by volume of tungsten filler, corresponding to about 1% to about 2% by weight of the filler.

The hard filler may be added to the fiber-forming polymer by any of the standard methods of adding a filler to a resin. For example, the combining of the hard filler and the fiber-forming polymer can be conveniently effected in an extruder, e.g., a twin screw extruder, by mixing the hard filler with molten polymer under conditions sufficient to provide a uniform distribution of the filler in the polymer. The hard filler may also be present during the manufacture of the fiber-forming polymer or may be added as the fiber-forming polymer is fed into the extruder of fiber-spinning equipment, in which case the blending and spinning steps are nearly simultaneous.

The cut-resistant fiber will preferably have a denier in the range of from about 1 to about 50 dpf, more preferably in the range of from about 2 to about 20 dpf, and most preferably from about 3 to about 15 dpf.

Cut-resistant fabric may be made by knitting or weaving the cut-resistant fiber using conventional methods and machinery. Non-woven fabrics can also be made. Such fabrics will have improved cut-resistance in comparison with the same fabric made using fiber manufactured from the same polymer without a filler. Generally, the cut-resistance will be improved by at least about 10% when measured using tests generally accepted in the industry for measuring cut-resistance (ASTM F1790), and preferably will be improved by at least about 20%, more preferably by at least about 35% and most preferably by at least about 50%.

Cut-resistant apparel may then be made from the cut-resistant fabric described above. For example, a cut-resistant safety glove designed for use in the food processing industries may be manufactured from the fabric. Such a glove is highly flexible and readily cleanable. The filled fiber resists flexural fatigue. Protective medical gloves may also be made using the cut-resistant fibers of this invention. These protective gloves can be sewn together from a fabric (woven, knit, or non-woven) made from the fibers and yarns taught herein. Alternatively, gloves can be knit directly from continuous yarns composed of the cut-resistant fiber, or pieces of fabric can be attached to gloves to protect the portions of the hand that are most at risk of being injured (e.g. palms or fingers).

The cut-resistant fiber and fabric made therefrom may also be used to form side curtains and tarpaulins for trucks, soft-sided luggage, commercial upholstery, inflatables, fuel cells, collapsible packaging, airline cargo curtains, firehose sheaths, cut-resistant aprons for use in metal packing, chaps, etc.

Other cut-resistant initial polymeric articles which can be coated with the cut-resistant coating in accordance with the present invention are cut-resistant tires, preferably lightweight tires such as bicycle tires. The cut-resistant coating is preferably disposed on those portions of the tire which come into contact with sharp objects such as sharp rocks, uneven terrain and the like. For example, the elastomeric material of the tire tread may be filled with hard particles such that the filled tread functions as the cut-resistant coating. In addition, the tire cord fibers can be filled with hard particles to resist cutting.

Examples of cut-resistant tires which can be used as the initial polymeric article in the present invention include those taught, for example, in U.S. Pat. Nos. 5,490,550; 5,327,954; and 4,436,130; each of the foregoing references being hereby incorporated by reference herein.

In other embodiments of the invention, the initial polymeric article may be a filled or unfilled nonwoven fabric.

A second aspect of the present invention is directed to a method of increasing the cut-resistance of an initial cut-resistant polymeric article involving the step of applying the above-described cut-resistant elastomeric coating to an outer surface of the above-described initial cut-resistant article, thereby forming a final polymeric article having improved cut-resistance. The final article of this invention has greater cut-resistance than a similar article coated with an elastomer which does not contain hard particles.

The elastomeric cut-resistant coating may be applied to the initial cut-resistant article conventional methods such as, e.g., dipping, spraying, flowing, rolling, brushing, partial coating, dotting, and strudeling in lines or zig-zag patterns, with dipping being more preferred. When the coating is applied to the initial article by dipping, the coating composition may be in the form of latex, solution, melt or any other liquid form capable of conversion in situ to a fully dried or cured coating. The initial article is dipped into the liquid coating composition and thereafter removed, carrying with it a coating of the elastomer and hard filler distributed in the elastomer. It may be desirable to allow the elastomer to dry or otherwise cure and thereafter repeat the dipping process a number of times to assure substantially complete coverage of the outer surface of the initial article with the coating.

In one preferred embodiment, the elastomeric coating will completely cover or substantially cover the outer surface of the initial article. In other preferred embodiments, the coating is disposed non-uniformly on the outer surface of the initial article as a partial coating, dots or strudeling in the form of lines or zig-zag patterns.

As stated previously herein, the polymeric articles provided by the present invention have improved cut-resistance, improved flexibility, and improved comfort and will retain their properties when laundered.

Also, elastomeric articles, such as surgeon's gloves, may also be coated with particle-filled elastomers to have more cut-resistance than the original article.

The following experiments illustrate but do not limit the present invention.

EXPERIMENTAL

Examples 1–6 and Comparative Example A

Examples 1–6 and Comparative Example A illustrate the effect of a hard filler, specifically, alumina, on the cut-resistance of a dried coating composition containing an elastomer, specifically polyvinyl chloride. The formulations of the coating compositions prepared in the examples are set forth in Table I below.

TABLE I

Comparative Example A and Examples 1–6: Formulations

| Example | Elastomer | Filler | Filler Concentration (wt. %) | Thickener |
|---|---|---|---|---|
| A | PVC | Alumina | 0 | no |
| 1 | PVC | Alumina | 5 | no |
| 2 | PVC | Alumina | 5 | no |
| 3 | PVC | Alumina | 5 | yes |
| 4 | PVC | Alumina | 10 | no |
| 5 | PVC | Alumina | 15 | yes |
| 6* | PVC | Alumina | 15 | yes |

*heat-cured at 150° F.

As indicated in Table I, the coating composition prepared in Comparative Example A contained no alumina, while the coating compositions prepared in Examples 1–6 contained varying amounts of alumina. The compositions prepared in Examples 3, 5 and 6 further contained a thickener. The composition prepared in Example 6 was heat-cured at a temperature of 150° F.

Cut-resistance of the coating compositions was measured using ASTM F1790. In this test, a sample of each of the dried coating compositions prepared in Comparative Example A and Examples 1–6 was placed on the flat surface of a mandrel. In each example, a series of tests was carried out in which a razor blade loaded with a variable weight was pulled across the coating sample until the sample was cut all the way through. The distance the razor blade traveled across the sample until the blade cut completely through the sample was measured. The point at which the razor blade cut through the sample was the point at which electrical contact was made between the mandrel and razor blade. The distance required to make the cut was plotted on a graph as a function of load on the razor blade The data was measured and plotted for cut distances varying from about 0.3 inches to about 1.8 inches. The resulting plot was approximately a straight line. An idealized straight line was drawn or calculated through the points on the plot, and the weight required to cut through the sample after one inch of travel across the sample was taken from the plot or calculated by regression analysis. In each example, the interpolated values of the weight required to make a cut after one inch of blade travel across the sample are shown in Table II below as "CPP", an abbreviation for Cut Protection Performance. For purposes of comparing the data for different thicknesses of the dried coating samples, the CPP value was divided by the thickness of the dried coating sample (OSY, which stands for ounces per square yard) to compensate for variations in coating thickness. This value is represented as CPP/OSY in Table II below.

TABLE II

Comparative Example A and Examples 1–6: Cut-resistance

| Example | OSY | CPP | CPP/OSY |
|---|---|---|---|
| A | 10 | 35 | 3.5 |
| 1 | 13 | 134 | 10.3 |
| 2 | 7.2 | 31 | 4.3 |
| 3 | 12 | 97 | 8.1 |
| 4 | 8.7 | 50 | 5.7 |
| 5 | 13 | 142 | 10.9 |
| 6 | 16 | 396 | 24.7 |

The data presented in Table II shows that the coating compositions containing the elastomer and the hard filler had better cut-resistance than the coating composition containing the elastomer but no hard filler.

What is claimed is:

1. A polymeric article having improved cut-resistance, comprising:
   (A) an initial polymeric article having initial cut-resistant properties; and
   (B) a cut-resistant elastomeric coating disposed on an outer surface of the initial polymeric article, wherein the elastomeric coating comprises an elastomer and a hard filler distributed in the elastomer, the hard filler having a Mohs Hardness value of at least about 3, thereby providing a final polymeric article having improved cut-resistant properties.

2. An article according to claim 1, wherein the hard filler has a Mohs Hardness value of at least about 4.

3. An article according to claim 1, wherein the hard filler is in the form of particles.

4. An article according to claim 3, wherein the hard filler is in the form of particles selected from the group consisting of platelet particles, needle particles, irregularly-shaped particles and round particles.

5. An article according to claim 3, wherein the hard particles have an average particle size of from about 1 to about 5 microns.

6. An article according to claim 1, wherein the coating comprises from about 1% to about 15% by weight of the hard filler.

7. An article according to claim 1, wherein the hard filler is selected from the group consisting of metals, metal alloys, ceramic materials and crystalline minerals.

8. An article according to claim 1, wherein the hard filler is alumina.

9. An article according to claim 1, wherein the elastomer is selected from the group consisting of a natural rubber, a synthetic rubber, and a thermoplastic elastomer.

10. An article according to claim 1, wherein the elastomer is selected from the group consisting of polyvinyl chloride, polyurethane, nitrile rubber, vinyl rubber, polyisoprene, neoprene, chloroprene and silicone rubber.

11. An article according to claim 1, wherein the elastomer is polyurethane, polyvinyl chloride or silicone rubber.

12. An article according to claim 1, wherein the coating has a thickness of from about 2 to about 3 millimeters.

13. An article according to claim 1, wherein the coating is disposed non-uniformly on the outer surface of the initial article.

14. An article according to claim 1, wherein the coating substantially or completely covers the outer surface of the initial article.

15. An article according to claim 1, wherein the initial article is a polymeric textile article.

16. An article according to claim 1, wherein the initial article is an elastomeric textile article.

17. An article according to claim 16, wherein the initial article is an elastomeric protective garment.

18. An article according to claim 17, wherein the initial article is a glove.

19. An article according to claim 18, wherein the glove is a surgical glove.

20. An article according to claim 1, wherein the article is a tire.

21. An article according to claim 1, wherein the initial polymeric article is a polymeric textile article made from a cut-resistant fiber which is formed from a fiber-forming polymer and a second hard filler distributed in the fiber-forming polymer.

22. An article according to claim 21, wherein the second hard filler has a Mohs Hardness value of at least about 3.

23. An article according to claim 21, wherein the second hard filler is selected from the group consisting of metals, metal alloys, ceramic materials and crystalline minerals.

24. An article according to claim 21, wherein the fiber-forming polymer is a liquid crystalline polymer or a melt-processable isotropic semi-crystalline polymer.

25. A method of improving cut-resistance properties of an initial cut-resistant polymeric article, comprising applying to an outer surface of the initial cut-resistant article a cut-resistant elastomeric coating comprising an elastomer and a hard filler distributed in the elastomer, the hard filler having a Mohs Hardness value of at least about 3, thereby forming a final polymeric article having improved cut-resistance.

26. A method according to claim 25, wherein the hard filler has a Mohs Hardness value of at least about 4.

27. A method according to claim 25, wherein the hard filler is in the form of particles.

28. A method according to claim 27, wherein the hard filler is in the form of particles selected from the group consisting of platelet particles, needle particles, irregularly-shaped particles and round particles.

29. A method according to claim 27, wherein the hard particles have an average particle size of from about 1 to about 5 microns.

30. A method according to claim 25, wherein the coating comprises from about 1% to about 15% by weight of the hard filler.

31. A method according to claim 25, wherein the hard filler is selected from the group consisting of metals, metal alloys, ceramic materials and crystalline minerals.

32. A method according to claim 25, wherein the hard filler is alumina.

33. A method according to claim 25, wherein the elastomer is selected from the group consisting of a natural rubber, a synthetic rubber, and a thermoplastic elastomer.

34. A method according to claim 25, wherein the elastomer is selected from the group consisting of polyvinyl chloride, polyurethane, nitrile rubber, vinyl rubber, polyisoprene, neoprene, chloroprene and silicone rubber.

35. A method according to claim 25, wherein the coating has a thickness of from about 2 to about 3 millimeters.

36. A method according to claim 25, wherein the coating is applied so as to be disposed non-uniformly on the outer surface of the initial article.

37. A method according to claim 25, wherein the coating is applied so as to substantially or completely cover the outer surface of the initial article.

38. A method according to claim 25, wherein the initial article is a polymeric textile article.

39. A method according to claim 25, wherein the initial article is an elastomeric textile article.

40. A method according to claim 39, wherein the article is an elastomeric protective garment.

41. A method according to claim 40, wherein the article is a glove.

42. A method according to claim 41, wherein the glove is a surgical glove.

43. A method according to claim 25, wherein the initial article is a tire.

44. A method according to claim 25, wherein the initial polymeric article is a polymeric textile article made from a cut-resistant fiber which is formed from a fiber-forming polymer and a second hard filler distributed in the fiber-forming polymer.

* * * * *